(12) United States Patent
Sakai et al.

(10) Patent No.: US 8,497,991 B2
(45) Date of Patent: Jul. 30, 2013

(54) THIN-FILM INSPECTION APPARATUS AND INSPECTION METHOD

(75) Inventors: Satoshi Sakai, Kanagawa (JP); Kohei Kawazoe, Nagasaki (JP); Kengo Yamaguchi, Nagasaki (JP); Akemi Takano, Nagasaki (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 101 days.

(21) Appl. No.: 13/120,319

(22) PCT Filed: Jul. 2, 2009

(86) PCT No.: PCT/JP2009/062118
§ 371 (c)(1),
(2), (4) Date: Apr. 19, 2011

(87) PCT Pub. No.: WO2010/097971
PCT Pub. Date: Sep. 2, 2010

(65) Prior Publication Data
US 2011/0194113 A1 Aug. 11, 2011

(30) Foreign Application Priority Data

Feb. 27, 2009 (JP) ................................ 2009-047359

(51) Int. Cl.
*G01N 21/47* (2006.01)
*G01N 21/00* (2006.01)

(52) U.S. Cl.
USPC ............... 356/432; 356/237.1; 356/237.4; 356/237.5

(58) Field of Classification Search
USPC ..... 356/237.1–237.5, 432–444, 239.1–239.3; 250/559.04, 559.41, 559.45
See application file for complete search history.

(56) References Cited

U.S. PATENT DOCUMENTS 3,814,946 A * 6/1974 Takahashi et al. ........ 250/559.45
5,452,079 A * 9/1995 Okugawa ................... 356/239.1
(Continued)

FOREIGN PATENT DOCUMENTS

CN 1554030 A 12/2004
JP S63-143830 6/1988
(Continued)

OTHER PUBLICATIONS

Chinese Patent Office, Office Action, Jul. 30, 2012.
(Continued)

*Primary Examiner* — Sang Nguyen
(74) *Attorney, Agent, or Firm* — Manabu Kanesaka; Kenneth M. Berner; Benjamin J. Hauptman

(57) ABSTRACT

An object is to reduce the effect of a film thickness variation on the substrate surface of a thin film and improve the measuring accuracy. Provided are a light source that radiates single-wavelength light to an inspection-target substrate (W), which is formed by forming a thin film on a glass substrate from the glass substrate side; a light receiving element that is disposed such that the light receiving axis intersects with the optical axis of illumination light emitted from the light source at a predetermined inclination angle and that receives diffused transmitted light that has been transmitted through the inspection-target substrate W; and a computer (7) that obtains a haze ratio of the thin film on the basis of the intensity of the light received by the light receiving element. The computer (7) has a haze ratio characteristic made by associating the haze ratio and the light intensity of the diffused transmitted light and obtains a haze ratio by using the haze ratio characteristic and the light intensity received by the light receiving element.

21 Claims, 12 Drawing Sheets

U.S. PATENT DOCUMENTS

| | | | |
|---|---|---|---|
| 5,539,514 A * | 7/1996 | Shishido et al. | 356/237.4 |
| 5,598,262 A * | 1/1997 | Jutard et al. | 356/239.1 |
| 5,691,811 A * | 11/1997 | Kihira | 356/239.1 |
| 6,628,379 B1 * | 9/2003 | Sudo et al. | 356/237.1 |
| 7,755,777 B2 * | 7/2010 | Sakai et al. | 356/632 |
| 8,027,036 B2 * | 9/2011 | Kim et al. | 356/337 |
| 2010/0033735 A1 * | 2/2010 | Sakai et al. | 356/632 |
| 2010/0177326 A1 * | 7/2010 | Sakai et al. | 356/632 |

FOREIGN PATENT DOCUMENTS

| | | |
|---|---|---|
| JP | 3017378 B | 3/1991 |
| JP | H03-163334 | 7/1991 |
| JP | H07-294429 | 11/1995 |
| JP | H09-273987 | 10/1997 |
| JP | 2001-356092 | 12/2001 |
| JP | 3341212 B2 | 11/2002 |
| JP | 2005-134324 | 5/2005 |
| JP | 2005-229076 | 8/2005 |
| JP | 2007-288043 | 11/2007 |
| JP | 2008-203090 | 9/2008 |
| JP | 2008-205188 | 9/2008 |

OTHER PUBLICATIONS

The State Intellectual Property Office of the People'S Republic of China, "Notification for Patent Registration Formalities for CN 200980138478.8", May 6, 2013.

* cited by examiner

FIG. 17

| SUBSTRATE ID | $\Delta Hz\,(1\sigma)$ |
|---|---|
| A | 1.4 |
| B | 1.6 |
| C | 1.4 |
| D | 1.2 |
| AVERAGE | 1.4 |

THIN-FILM INSPECTION APPARATUS AND INSPECTION METHOD

RELATED APPLICATIONS

The present application is National Phase of International Application No. PCT/JP2009/062118 filed Jul. 2, 2009, and claims priority from Japanese Application No. 2009-047359 filed Feb. 27, 2009, the disclosure of which is hereby incorporated by reference herein in its entirety.

TECHNICAL FIELD

The present invention relates to a thin-film inspection apparatus and inspection method for inspecting the film quality of a thin film formed on a glass substrate, for example, a transparent conductive film formed on a transparent glass substrate of a solar cell.

BACKGROUND ART

For example, in a solar cell, a transparent conductive film is formed on a transparent glass substrate made of soda lime glass etc. Irregularities are formed intentionally on the surface of this transparent conductive film in order to achieve a light trapping effect. The size of the irregularities is, for example, about 0.3 μm in relation to a film thickness of 0.8 μm. In the related art, the haze ratio is used as a feature quantity for evaluating such surface irregularities of such a transparent conductive film.

As a method for determining this haze ratio, for example, a technique disclosed in PTL 1 is known. PTL 1 discloses a method for calculating the haze ratio of a transparent conductive film by irradiating the transparent conductive film with light, dispersing the reflected light into at least two wavelengths, and computing the light intensities of these wavelengths.

In addition, PTL 1 discloses that it is possible to build a device for calculating the haze ratio into a production line for inspecting all of the solar cells having a transparent conductive film.

CITATION LIST

Patent Literature

{PTL 1}
Japanese Unexamined Patent Application, Publication No. 2005-134324

SUMMARY OF INVENTION

Technical Problem

If the film thickness of the transparent conductive film is not uniform and the film thickness varies across the film surface, the desired accuracy may not be satisfied when evaluating the transparent conductive film using the above-described apparatus because of interference fringes added on the reflection spectrum.

The present invention has been made in view of these circumstances, and an object thereof is to provide a thin-film inspection apparatus and inspection method that is capable of reducing the effects of variations of the film thickness across the substrate surface of the thin film, thereby allowing improved measuring accuracy.

Solution to Problem

In order to solve the above-described problems, the present invention employs the following solutions.

A first aspect of the present invention is a thin-film inspection apparatus, including: a light source that radiates single-wavelength light to an inspection-target substrate, which is formed by forming a thin film on a glass substrate from the glass substrate side; a light receiving section that is disposed such that a light receiving axis intersects with an optical axis of illumination light emitted from the light source at a predetermined inclination angle and that receives diffused transmitted light that has been transmitted through the inspection-target substrate; and a processor that obtains a haze ratio of the thin film on the basis of an intensity of light received by the light receiving section; wherein the processor has a haze ratio characteristic that is made by associating the haze ratio and the light intensity of the diffused transmitted light and obtains the haze ratio by using the haze ratio characteristic and the intensity of the light received by the light receiving section.

According to this aspect, since single-wavelength light is radiated from the glass substrate side of the inspection-target substrate, the diffused transmitted light at that time is received by the light receiving section, and the haze ratio of the thin film is obtained on the basis of the intensity of the light received, it is possible to obtain the haze ratio without being affected by film thickness as in the related art.

Therefore, it is possible to suppress the measurement errors due to the film thickness variations and to improve the measuring accuracy of the haze ratio.

"Single-wavelength light" mentioned above means light whose wavelength band of the fundamental wavelength is about 100 nm or less, and desirably 50 nm or less, full width at half maximum, and includes light emitted from light emitting devices such as LEDs etc.

In the above-mentioned thin-film inspection apparatus, the light source may be disposed such that the optical axis of the illumination light emitted from the light source matches a normal direction of the inspection-target substrate.

In the above-mentioned thin-film inspection apparatus, the light source may emit light having any wavelength from 350 nm or more to 760 nm or less, preferably any wavelength from 350 nm or more to 590 nm or less. By using such wavelengths, it is possible to ensure the measuring accuracy of stable haze ratios.

In the above-mentioned thin-film inspection apparatus, preferably, when the light source emits light having any wavelength from 470 nm or more to 590 nm or less, an inclination angle of the light receiving section relative to the substrate surface of the inspection-target substrate may be from 54° or more to 65° or less.

By doing so, the measuring accuracy of the haze ratio can be increased further.

In the above-mentioned thin-film inspection apparatus, a first light shielding section may be attached to the light source, and a second light shielding section may be attached to the light receiving section.

By attaching a first light shielding section and a second light shielding section in such a manner, it is possible to prevent the entry of light from the outside and to achieve a superior inspection environment.

In the above-mentioned thin-film inspection apparatus, in a case where a plurality of test pieces, which are formed by forming thin films having different haze ratios on glass substrates, are provided; the diffused transmitted light when the test piece is shifted vertically by a predetermined amount in an optical axial direction of the illumination light is received by the light receiving section; and when the haze ratio characteristic is made by associating the light intensity and the haze ratio, the light receiving section is preferably disposed at an inclination angle such that a relationship between the haze ratio and the light intensity is expressed as a monotonic increase or a monotonic decrease within a range of the haze ratios of the thin film to be inspected, and an amount of change in the haze ratio characteristic due to a vertical shift of a mounting position of the test piece becomes a predetermined value or less.

When an apparatus for calculating the haze ratio is built into the production line, in order to realize inspection of all substrates without delay, since it is required to measure the haze ratio while transporting the inspection-target substrate, on which a thin film is formed, it is important to assemble a measurement system that is robust against a vertical shift (shift of the workpiece) of the inspection-target substrate due to the transportation. This is because, as described above, since the haze ratios are obtained by computing the light intensities, it can be considered that the variation of the signal level due to the vertical shift of the substrates is directly linked to the measurement error of the haze ratio, and it lowers the determination accuracy.

According to the above-described aspect, since the inclination angle of the light receiving section is determined by considering such vertical vibrations of the inspection-target substrate, even when the apparatus is built into an actual production line and used, it is possible to obtain highly reliable measurement results without being influenced by the vertical shift of the substrate.

In the above-mentioned thin-film inspection apparatus, when an inclination angle of the light receiving section, a size of an aperture at a light emitting side of the first light shielding section, a length from a tip of the light source to a tip of a light emitting end, a size of an aperture opposite the light receiving section in the second light shielding section, a length from a light receiving surface of the light receiving section to a tip of the aperture, and a distance from a position on an upper surface of the inspection-target substrate through which the optical axis of the illumination light passes to the light receiving surface of the light receiving section are each set as arrangement parameters, these arrangement parameters are preferably determined such that, in a case where a plurality of test pieces, which are formed by forming thin films having different haze ratios on glass substrates, are provided; the diffused transmitted light when the test piece is shifted vertically by a predetermined amount in an optical axial direction of the illumination light is received by the light receiving section; and the haze ratio characteristic is made by associating the light intensity and the haze ratio; a relationship between the haze ratio and the light intensity is expressed as a monotonic increase or a monotonic decrease within a range of the haze ratio of the thin film to be inspected, and a maximum value of an amount of change in the light intensity due to a vertical shift of a mounting position of the test piece becomes a predetermined value or less.

According to such an aspect, since the values of the respective arrangement parameters are determined by taking the vertical shift of the inspection-target substrate into consideration, even when the apparatus is built into an actual production line and used, it is possible to obtain highly reliable measurement results without being influenced by the vertical shift of the inspection-target substrate.

The above-mentioned thin-film inspection apparatus may be built into a thin-film production line, and the light source may be disposed at a position for radiating the illumination light to the inspection-target substrate, which is transported in the production line, from the glass substrate side.

A second aspect of the present invention is a thin-film production system that inspects the thin film of the inspection-target substrate including any of the above-mentioned thin-film inspection apparatus, wherein the light source is disposed so as to radiate light to the inspection-target substrate, which is transported in a production line, from the glass substrate side.

A third aspect of the present invention is a thin-film inspection method including steps of providing a haze ratio characteristic made by associating a light intensity of diffused transmitted light and a haze ratio of a thin film in advance; radiating single-wavelength light to an inspection-target substrate, which is formed by forming a thin film on a glass substrate from a glass substrate side; receiving the diffused transmitted light that has passed through the inspection-target substrate; and obtaining the haze ratio of the thin film by using the intensity of the light received and the haze ratio characteristic.

A fourth aspect of the present invention is a method for determining arrangement of a measurement system applied to the above-mentioned thin-film inspection apparatus including when a wavelength of the light source, an inclination angle at which the light receiving section is disposed, a size of an aperture at a light emitting side of the first light shielding section, a length from a tip of the light source to a tip of a light emitting end, a size of an aperture opposite the light receiving section in the second light shielding section, a length from the light receiving surface of the light receiving section to a tip of the aperture, and a distance from a position on an upper surface of the inspection-target substrate through which the optical axis of the illumination light passes to a light receiving surface of the light receiving section are set as arrangement parameters, a first step in which a plurality of test pieces, which are formed by forming thin films having different haze ratios on glass substrates are provided; a second step in which, in the measurement system where the parameters are varied within predetermined ranges, each of which has been determined for every parameter, the diffused transmitted light is received by the light receiving section when the test pieces are shifted vertically by a predetermined amount in an optical axial direction of the illumination light; a third step in which haze ratio characteristics are made by associating the light intensity of the diffused transmitted light and the haze ratio obtained in the second step, and these haze ratio characteristics are associated with respective parameter set values of the measurement system when the haze ratio characteristics are obtained; a fourth step in which a haze ratio characteristic is extracted from a plurality of the haze ratio characteristics made in third step, such that a relationship between the haze ratio and the light intensity is expressed as a monotonic increase or a monotonic decrease within a range of the haze ratio of the thin film to be inspected, and a maximum value of an amount of change in the light intensity due to a vertical shift of a mounting position of the test piece is a predetermined value or less; and a fifth step in which the parameters when the haze ratio characteristic that is extracted in fourth step is obtained are employed as the arrangement parameters of the measurement system in the inspection.

By determining the respective arrangement parameters of the measurement system using such a method for determining the arrangement of the measurement system, even when the thin-film inspection apparatus is built into a production line, it is possible to assemble a measurement system that is robust against the vertical vibration of an inspection-target substrate.

Advantageous Effects of Invention

According to the present invention, it is possible to reduce the effect of the variation in film thickness across the substrate surface of the thin film; therefore, improved measuring accuracy can be achieved.

BRIEF DESCRIPTION OF DRAWINGS

FIG. 17 is a figure showing the effects of a thin-film inspection apparatus according to an embodiment of the present invention.

DESCRIPTION OF EMBODIMENTS

An embodiment where a thin-film inspection apparatus and method according to the present invention is applied to evaluating a transparent conductive film of a solar cell will be described below, with reference to the drawings.

Figure 1:
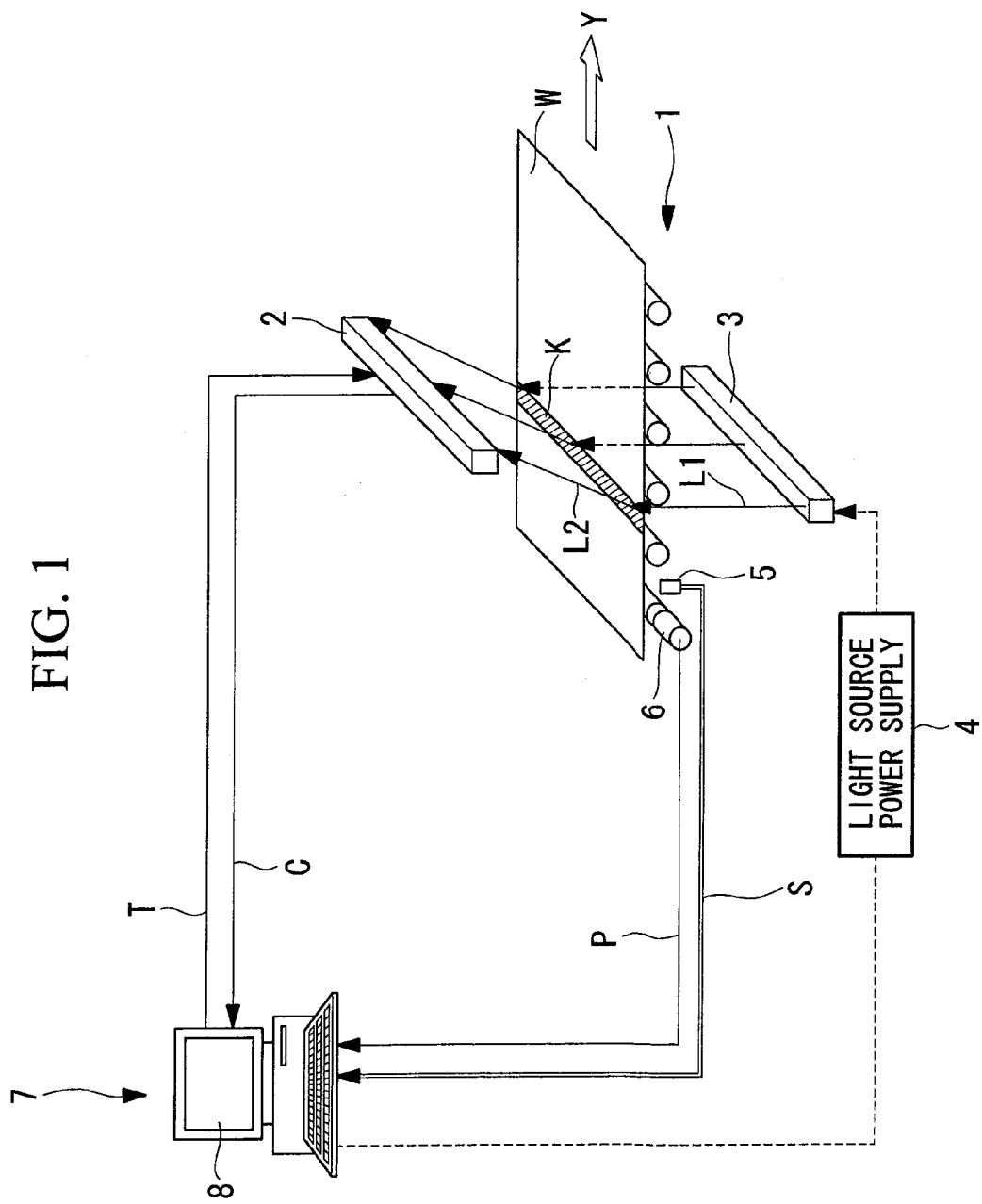
FIG. 1 is a diagram showing the overall configuration of thin-film inspection apparatus according to an embodiment of the present invention.

FIG. 1 is a diagram showing the overall configuration of a thin-film inspection apparatus according to an embodiment of the present invention. As shown in FIG. 1, the thin-film inspection apparatus according to this embodiment is utilized by being mounted in a production line of solar cell fabrication equipment. An inspection-target substrate W that is to be inspected by the thin-film inspection apparatus is a glass substrate with a transparent conductive film in which a transparent conductive film (TCO: Transparent Conductive Oxide) made of ITO (indium tin oxide), zinc oxide (ZnO), tin oxide ($SnO_2$), and so forth is formed on a transparent glass substrate of about 1 m square. This inspection-target substrate W is transported such that the transparent conductive film faces up. In order to avoid diffusion at the glass substrate interface, an $SiO_2$ film etc. may be formed as an underlying film between the transparent conductive film and the glass substrate.

A light radiating apparatus 3 and a photoreceptor 2 are disposed below and above a transport conveyor 1 for transporting the inspection-target substrate W, respectively. The light radiating apparatus 3 is provided with, for example, a plurality of light sources 3a disposed linearly along the width direction of the inspection-target substrate W (see FIG. 2). In this embodiment, eight light sources 3a are disposed. Here, single-wavelength LEDs, or white LEDs that use combinations of filters, etc. may be used as the light sources 3a. In addition, the light sources 3a are not limited to LEDs; other light sources, for example, lamp light sources, light source units in which lamp light sources and filters are combined, and so forth may be used. As the wavelength of light emitted from the light radiating apparatus 3, the wavelength selected by the parameter setting method described later is used.

With the light radiating apparatus 3, adjustment of the amount of light and on/off control of the light sources are performed by operating a light source power supply 4 based on signals sent from a computer 7 described later.

Diffused transmitted light L2 is received by the photoreceptor 2 by transmitting the emitted light L1 emitted from each of the light sources 3a provided in the light radiating apparatus 3 through the inspection-target substrate W. The photoreceptor 2 has, for example, a plurality of light receiving elements (light receiving sections) 2a disposed linearly along the width direction of the inspection-target substrate W (see FIG. 2). In this embodiment, eight light receiving elements 2a are disposed. The light receiving elements 2a and the light sources 3a are disposed to form pairs such that the diffuse transmitted light of the illumination light emitted form the corresponding light source 3a is received by the light receiving element 2a. The light receiving elements 2a can be elements etc. that are sensitive to the wavelengths of the light to be measured, and they can be configured simply and cost effectively by using, for example, photodiodes, photomultiplier tubes, and so forth. At this time, it is desirable that the light receiving elements 2a be adjusted such that they exhibit substantially uniform detection sensitivities when the inspection-target substrate W is not present. In addition, for example, it is preferable that the light receiving elements 2a be calibrated such that the signal strength becomes substantially zero when the inspection-target substrate W is not present, or calibrated such that the signal strength becomes 100% when the illumination light is received when the light receiving elements 2a are positioned on the optical axis of the illumination light.

Figure 2:
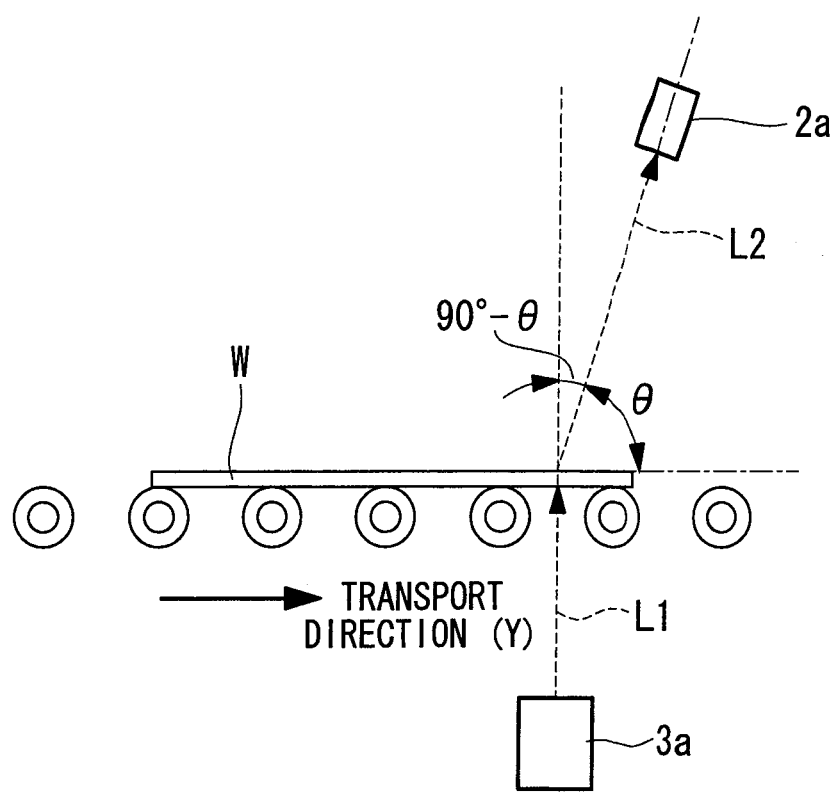
FIG. 2 is a diagram showing the positional relationship of a light source and a light receiving element.

FIG. 2 shows the positional relationship of the light sources 3a and the light receiving elements 2a. As shown in FIG. 2, the illumination light L1 emitted from the light source 3a enters perpendicular to the substrate surface of the inspection-target substrate W, in other words, in the normal direction from the substrate surface. This illumination light L1 is diffused within the film and at the surface of the film of the inspection-target substrate W, and part of the diffused transmitted light is received by the light receiving element 2a. The light receiving element 2a is disposed such that the light receiving axis intersects with the optical axis of the illumination light L1 emitted from the light source 3a at a predetermined inclination angle of (90°-θ) and receives the diffused transmitted light L2 that has been transmitted through the inspection-target substrate W.

The inclination angle θ, selected by the parameter setting method described later, is used for the inclination angle θ of the light receiving elements 2a.

Referring back to FIG. 1, the transport conveyor 1 is provided with a photoelectric switch 5 and a rotary encoder 6. The photoelectric switch 5 generates inspection start signals S and sends them to the computer 7 when the tip portion of the inspection-target substrate W being transported is detected to reach the incident position of the illumination light L1. The rotary encoder 6 generates pulse signals P and sends them to the computer 7 at every set rotation angle, in other words, every time the inspection-target substrate W moves by a set distance.

After receiving the inspection start signals S, the computer (processor) 7 sends trigger signals T to the photoreceptor 2 in response to the respective pulse signals P received. Each of the light receiving elements 2a of the photoreceptor 2 receives, in response to the respective trigger signals T received, the diffused transmitted light L2 that has passed through the inspection-target substrate W and sends photoreceiver signals C corresponding to the light intensities to the computer 7.

After receiving the photoreceiver signals C from each of the light receiving elements 2a of the photoreceptor 2, the computer 7 calculates the haze ratios of the inspection-target substrate W by using the light intensities of the diffused transmitted light, which are indicated by these photoreceiver signals C, and previously stored haze ratio characteristics (haze ratio versus light intensity calibration characteristics).

Figure 3:
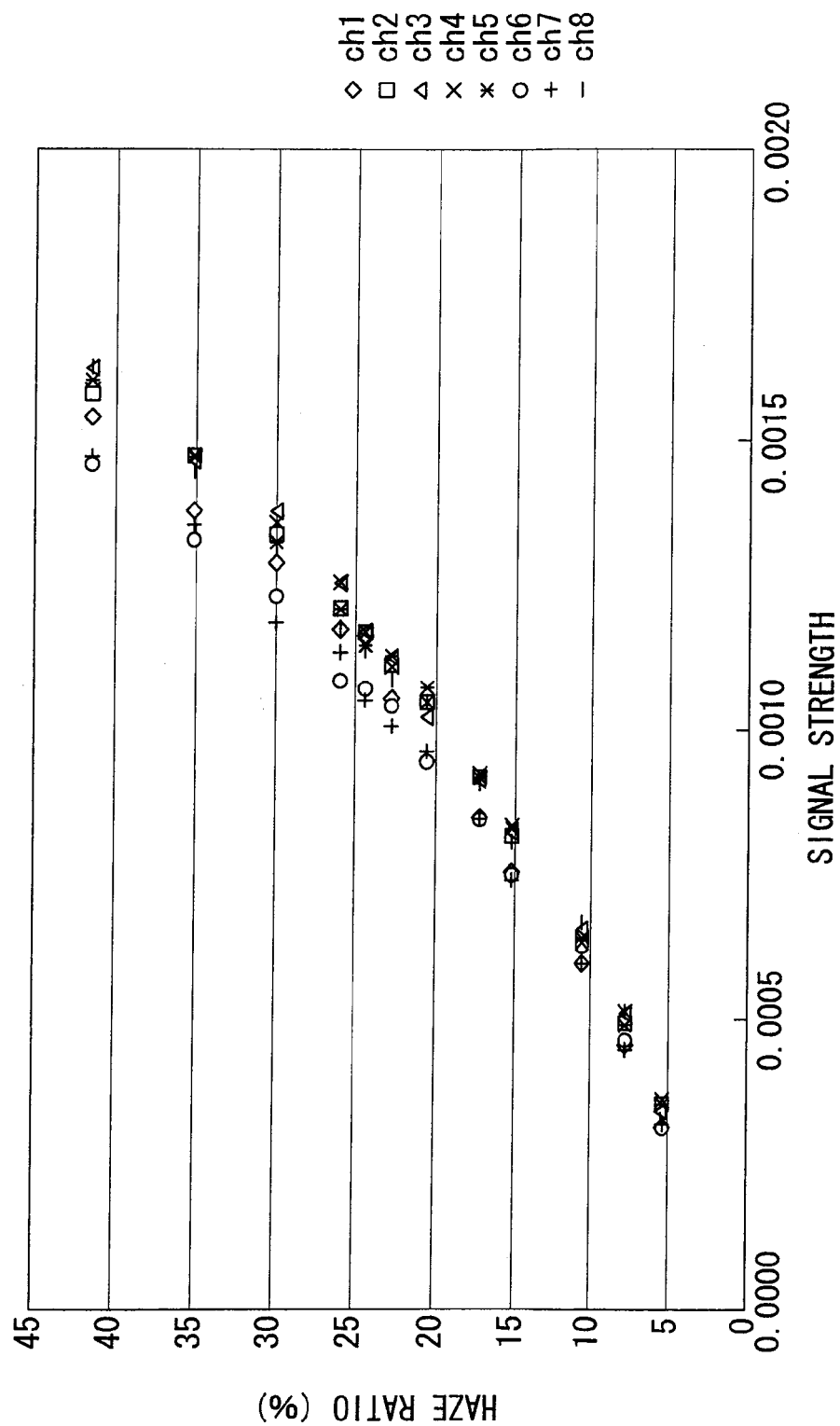
FIG. 3 is a figure showing an example of haze ratio characteristics stored in a computer.

FIG. 3 shows an example of haze ratio characteristics. In FIG. 3, the horizontal axis indicates the signal strength (the light intensity of the diffused transmitted light) and the vertical axis indicates the haze ratio. FIG. 3 shows a case in which each of the light receiving elements has the haze ratio characteristic. By having the haze ratio characteristic that correspond to the respective light receiving elements in this manner, it is possible to obtain the haze ratios in which the characteristic of the respective light receiving elements has been taken into account; and therefore, it is possible to improve the detection accuracy even more. In addition, although the light intensity is indicated on the horizontal axis and the haze ratio is indicated on the vertical axis in FIG. 3, the haze ratio and the light intensity may be indicated on the horizontal axis and the vertical axis, respectively. The haze ratio characteristic refers to a characteristic that indicates the relationship between the haze ratio and the light intensity of the diffused transmitted light; for example, JIS K 7136 describes the haze ratio as "defined as the ratio of total light transmittance $\tau_t$ to the diffuse transmittance $\tau_d$".

The haze ratio characteristics that are shown in FIG. 3 and stored in the computer 7 are made by providing a plurality of test pieces having known haze ratio; with the same measurement system as the actual inspection apparatus shown in FIG. 1, receiving the diffused transmitted light from the light radiated to these test pieces with the respective light receiving elements 2a; and correlating the light intensities received by the respective light receiving elements 2a with the known haze ratio at that time.

Figure 4:
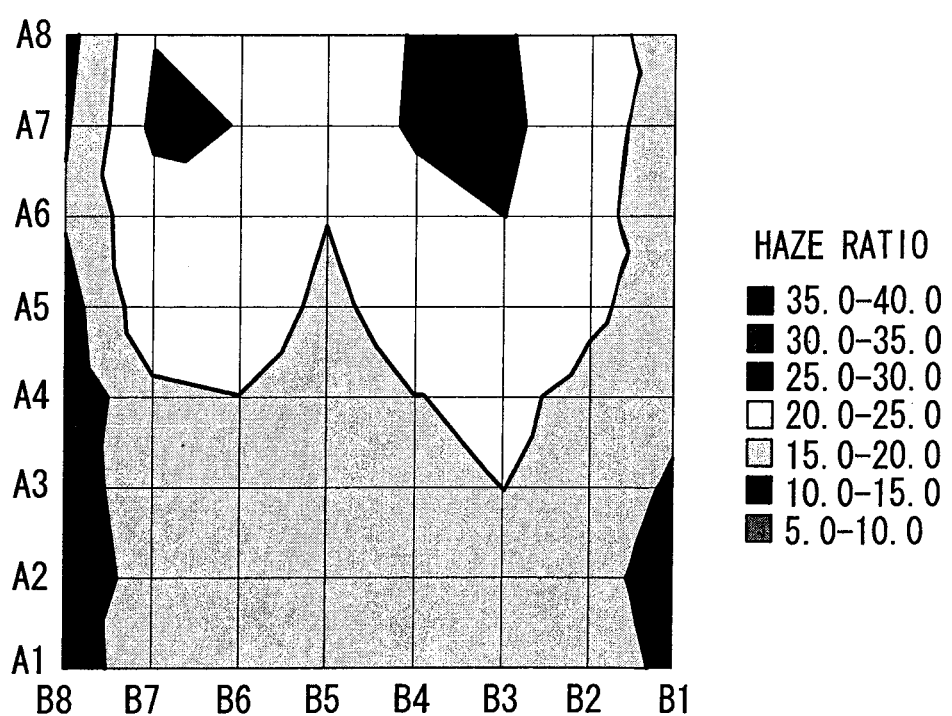
FIG. 4 is a figure showing an example of a two-dimensional distribution image of haze ratios that are displayed as measurement results.

The computer 7 obtains the haze ratios from the light intensities received by the respective light receiving elements 2a using the previously stored haze ratio characteristic, and then stores the haze ratios in a memory section (not shown) by associating them with the inspection positions on the inspection-target substrate W based on the timings at which the diffused transmitted light is received by the respective light receiving elements 2a. By doing so, after the inspection of one inspection-target substrate W is finished, by reading out the haze ratios for the respective inspection positions that are stored in the memory section, it is possible to make a two-dimensional distribution image of the haze ratios, as shown in FIG. 4, and to display it on a display device 8. In addition, it is possible to employ an aspect in which an allowable range for the haze ratio is stored in advance and an error is reported when a haze ratio outside this allowable range is detected.

Next, the case where inspection of the haze ratios of the transparent conductive film is performed by the thin-film inspection apparatus shown in FIG. 1 will be described. Here, the case where the haze ratios of the transparent conductive film are calculated by radiating the light having the wavelength λ1 to the inspection-target substrate W. In this case, the haze ratio characteristic corresponding to the wavelength λ1 is stored in advance in the memory section (not shown) provided in the computer 7.

First, the computer 7 causes the inspection-target substrate W, which is placed on the transport conveyor 1, to be transported in the transport direction Y, while keeping each of the light sources of the light radiating apparatus 3 on. By doing so, the illumination light L1 emitted from the light radiating apparatus 3 is transmitted through the inspection-target substrate W and is diffused thereby, and the diffused transmitted light L2 that is part of the diffused light transmitted is guided to the photoreceptor 2.

On the other hand, the pulse signals P are sent to the computer 7 from the rotary encoder 6 according to the movement of this inspection-target substrate W. The computer 7 sends the trigger signals T to the photoreceptor 2 in response to the respective pulse signals P received. Thereby, the diffused transmitted light L2 is received by each of the light receiving elements 2a of the photoreceptor 2 according to the movement of the inspection-target substrate W, and the photoreceiver signals C according to the light intensities are sent to the computer 7. After receiving the photoreceiver signals C from respective light receiving elements 2, the computer 7 obtains the haze ratios from the photoreceiver signals C and the haze ratio characteristic, and stores the haze ratios in the memory section. By doing so, it is possible to calculate the haze ratios at respective measuring positions on the inspection-target substrate W and to obtain the haze ratio distribution in the inspection-target substrate W.

Next, a wavelength selection method for selecting the wavelength of the light used for the measurement of the haze ratios, in the thin-film inspection apparatus shown in FIG. 1, will be described.

First, a plurality of test pieces, which are formed by forming transparent conductive films having different haze ratios on glass substrates are provided. It is desired that the test pieces provided at this time have substantially the same film configuration as the inspection-target substrate W for the actual haze ratio measurement. In this embodiment, test pieces having haze ratios of 18%, 20%, and 29%, respectively, are provided.

Next, light having a wavelength of 300 nm to 1500 nm is made incident on thus-provided test pieces from the glass substrate side perpendicularly to the film surface of the glass substrate, and the diffused transmitted light at that time is detected by using an integrating sphere, thereby conducting measurement of the transmitted light flux. This measurement is performed by a measuring device in which an integrating sphere of 60 mm diameter is attached to a U-3500 Spectrophotometer manufactured by Hitachi, Ltd. First of all, a white plate is disposed at the light emitting position in the integrating sphere to perform calibration of a 100% baseline. Next, the white plate is removed and the test piece is disposed at the light incident position in the integrating sphere such that the glass substrate side becomes the light-incident surface. In this state, dispersed light is radiated to the test piece, only the forward-scattered light excluding the vertical transmitted light is measured by the photoreceiver that is built into the integrating sphere, and the diffuse transmittance is obtained.

Figure 5:
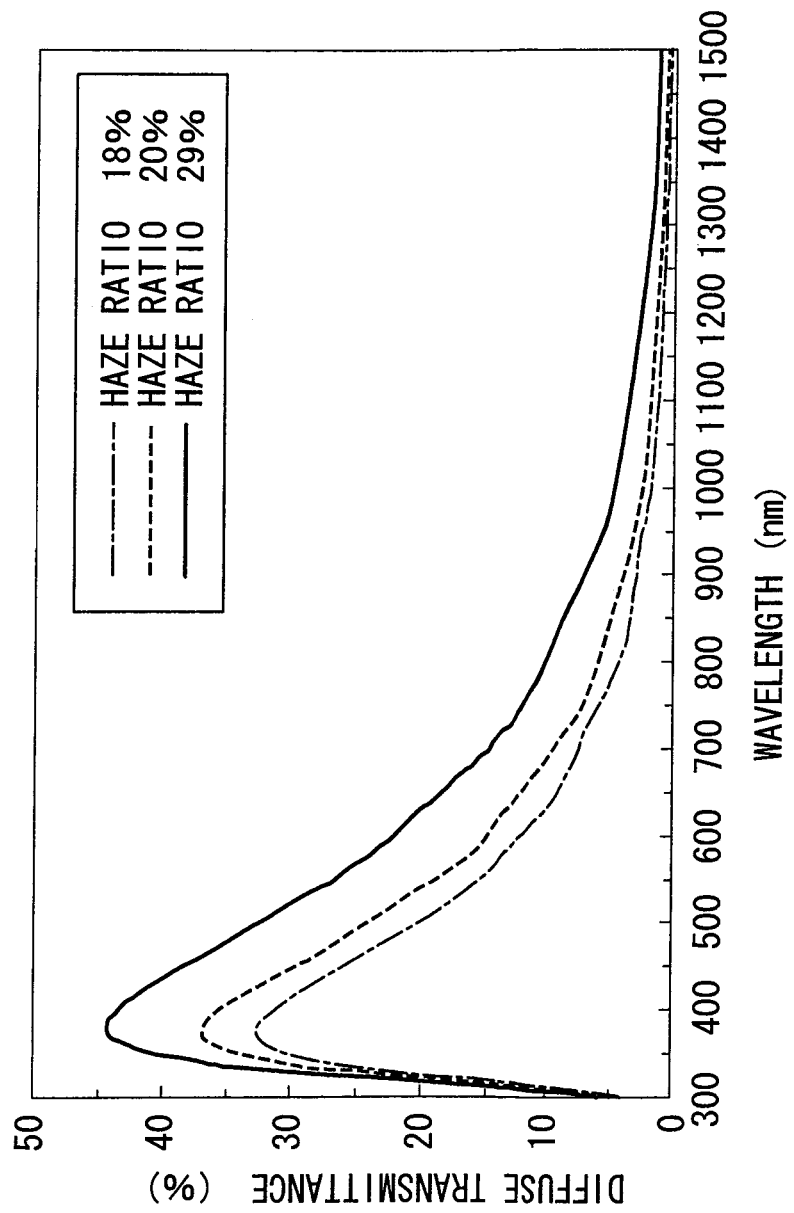
FIG. 5 is a figure showing diffuse transmission spectra (wavelength ranging from 300 nm to 1500 nm) of test pieces having different haze ratios.

FIG. 5 shows the relation between the wavelength and the diffuse transmittance in the respective test pieces.

As shown in FIG. 5, the diffuse transmittance shows a peak at around the wavelength of 350 nm, and thereafter, the diffuse transmittance gradually decreases exponentially as the wavelength becomes longer. The higher the diffuse transmittance, the higher the light intensity detected by the light receiving elements 2a in the apparatus shown in FIG. 1 becomes; therefore, it means that stable detection accuracy tends to be achieved. Thus, it is preferable that the wavelengths to be used as the light source be those that result in high light intensities. In addition, since installation and/or adjustment of the light source, the light receiving elements, and so forth are performed visually by the operator, visible light is preferred from the viewpoint of operability.

From these viewpoints, in FIG. 5, it is found out that it is preferable to use light having a wavelength ranging from 350 nm or more to 760 nm or less. In addition, the peak around 350 nm is known to shift according to the properties of the transparent glass substrate used. In addition, commercially sold LEDs are cheap and are also advantageous in terms of convenience. Therefore, it is preferred to use LEDs having wavelengths of, for example, 450 nm, 470 nm, 530 nm, 560 nm, 570 nm, 590 nm, 644 nm, 660 nm, 700 nm, and so forth as the light sources.

In addition, for the haze ratio measurement defined in JIS K 7136, white light that has been transmitted through a y filter that substantially achieves a center wavelength of about 550 nm is used as the illumination light. In JIS K 7136, the y filter is defined as "spectral luminous efficiency for photopic vision $V(\lambda)$ equivalent to a color matching function $y(\lambda)$ according to ISO/CIE 10527".

Thus, it is also advantageous to use 550 nm light as the illumination light. In addition, in the test described later, by using the 590 nm illumination light and evaluating its suitability, the appropriate haze ratio characteristics are obtained even with the 590 nm illumination light, and it has been demonstrated that measurement with high reliability is achieved. Therefore, for example, the wavelength to be used as the light source is preferably set at 300 nm, and more preferably at about from 350 nm or more to about 590 nm or less, where the peak of the diffuse transmittance occurs. As shown in FIG. 5, since relatively high diffuse transmittance can be obtained in this wavelength band, stable measuring accuracy can be ensured.

[First Parameter Setting Method]

Next, as shown in FIG. 1, the thin-film inspection apparatus according to this embodiment is built into the production lines and inspects the inspection-target substrates W being transported. Therefore, the inspection-target substrates W are expected to vibrate in the vertical direction, and it is important to assemble a measurement system that is robust against such vertical movements.

Thus, in this embodiment, in the wavelength band ranging from 350 nm or more to 760 nm or less, the wavelengths of 470 nm, 530 nm, and 590 nm are selected as the representative wavelengths among the wavelengths that correspond to the wavelengths of commercial LEDs, which are available cheaply, and arrangement parameters for a measurement system that is robust against the vertical vibration of the inspection-target substrates W are obtained.

Figure 6:
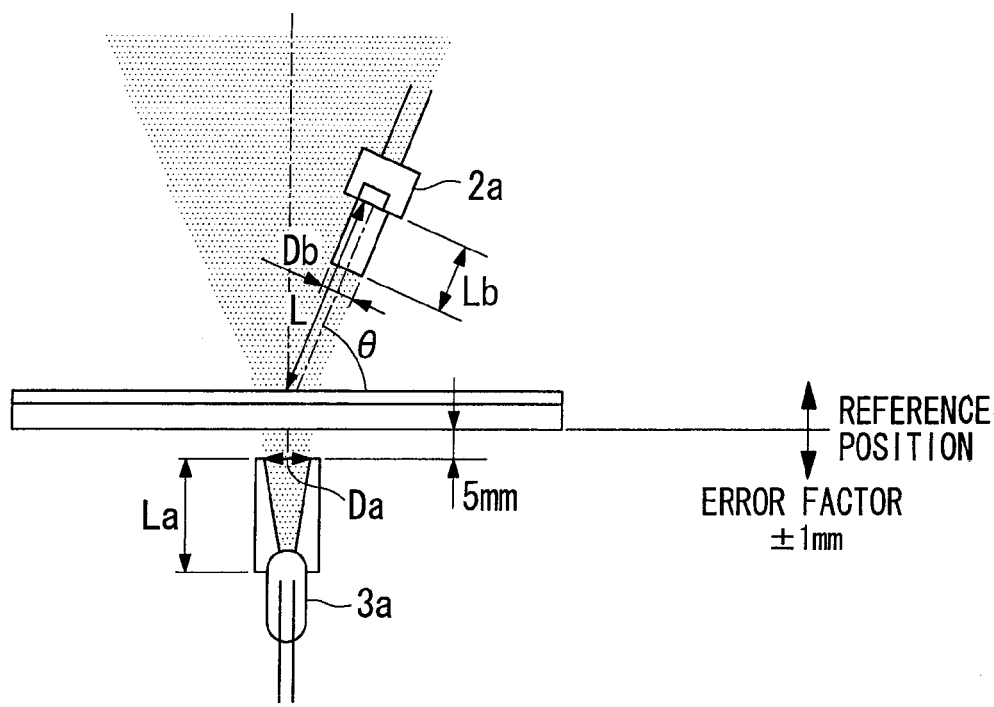
FIG. 6 is a diagram for explaining the configuration and arrangement parameters of a measurement system.

In addition, in this embodiment, in order to prevent the entry of light from the outside, a tubular light shielding hood is attached to the light source (LED) 3a and the light receiving elements 2a. The shape of the light shielding hood is not specifically limited. As shown in FIG. 6, the following six arrangement parameters for the measurement system are set: the height La of the tubular light shielding hood of the light source 3a; the tube diameter Da of the light shielding hood of the light source 3a; the distance L from the point on the film surface of the transparent conductive film through which the optical axis of the illumination light passes to the light receiving surface of the light receiving element 2a; the length Lb of the tubular light shielding hood of the light receiving element 2a; the tube diameter Db of the tubular light shielding hood of the light receiving element 2a; and the inclination angle θ of the light receiving element 2a.

In addition, the variation range of the respective arrangement parameters is set as in the following table.

TABLE 1

| | Range | |
|---|---|---|
| | Minimum value | Maximum value |
| Da (mm) | 5 | 7 |
| θ (°) | 54 | 65 |
| λ (nm) | 470 | 590 |
| L (mm) | 25 | 40 |
| La (mm) | 5 | 15 |
| Lb (mm) | 5 | 15 |
| Db (mm) | 5 | 10 |

Next, a plurality of haze ratio characteristics are made by: providing test pieces, which are formed by forming the transparent conductive films with different haze ratios on the transparent substrates (specifically, ten test pieces having haze ratios of 7.9%, 10.6%, 15.3%, 17.4%, 20.5%, 22.8%, 24.5%, 26.1%, 29.8%, and 35.1% are provided); arranging these test pieces so as to be positioned 5 mm away from the tip of the light shielding hood of the light source 3a (this position is referred to as "reference position"), and such that the illumination light emitted from the light source 3a enters perpendicularly; in this state, measuring the light intensities that are detected by the light receiving elements 2a by varying the above-mentioned arrangement parameters within the variation range; and correlating the light intensities and the known haze ratios of the test pieces.

Next, in the measurement system shown in FIG. 6, the intensities of the light received by the light receiving elements 2a are measured in situations where the position of the test piece is shifted towards the substrate surface by −1 mm and +1 mm, respectively, from the reference position in the vertical direction, and the haze ratio characteristics are made by correlating the light intensities and the known haze ratios of the test pieces.

Figure 7:
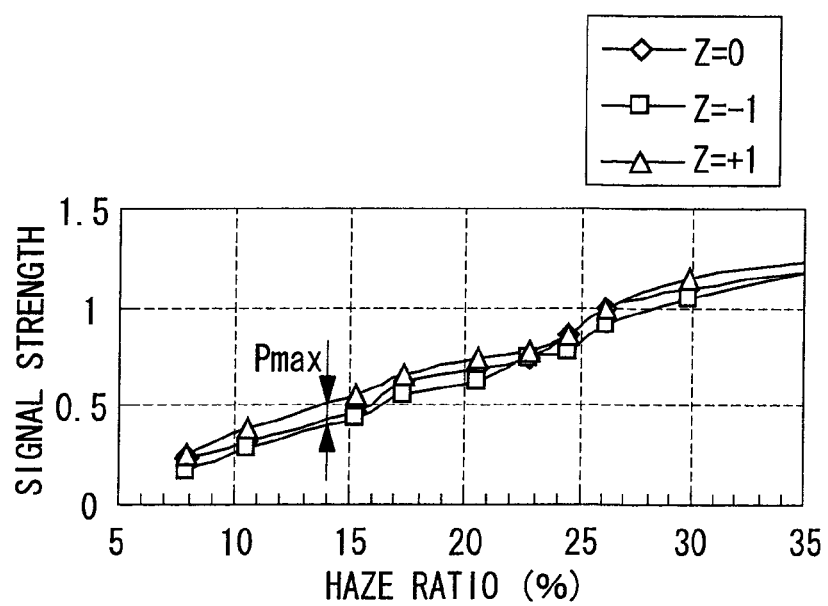
FIG. 7 is a figure showing haze ratio characteristics obtained by a preliminary test conducted for determining arrangement parameters.
Figure 8:
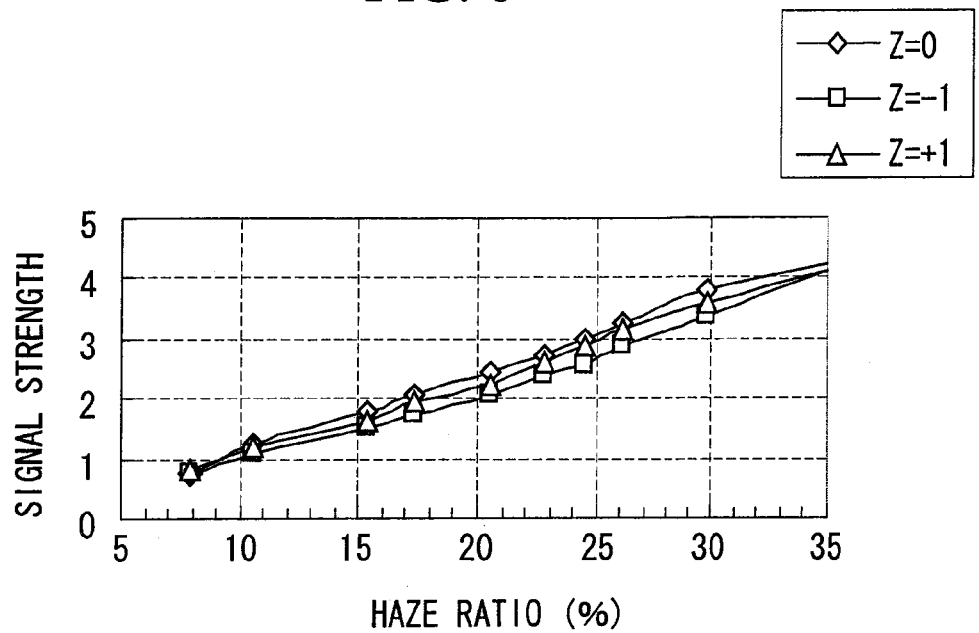
FIG. 8 is a figure showing haze ratio characteristics obtained by a preliminary test conducted for determining arrangement parameters.
Figure 9:
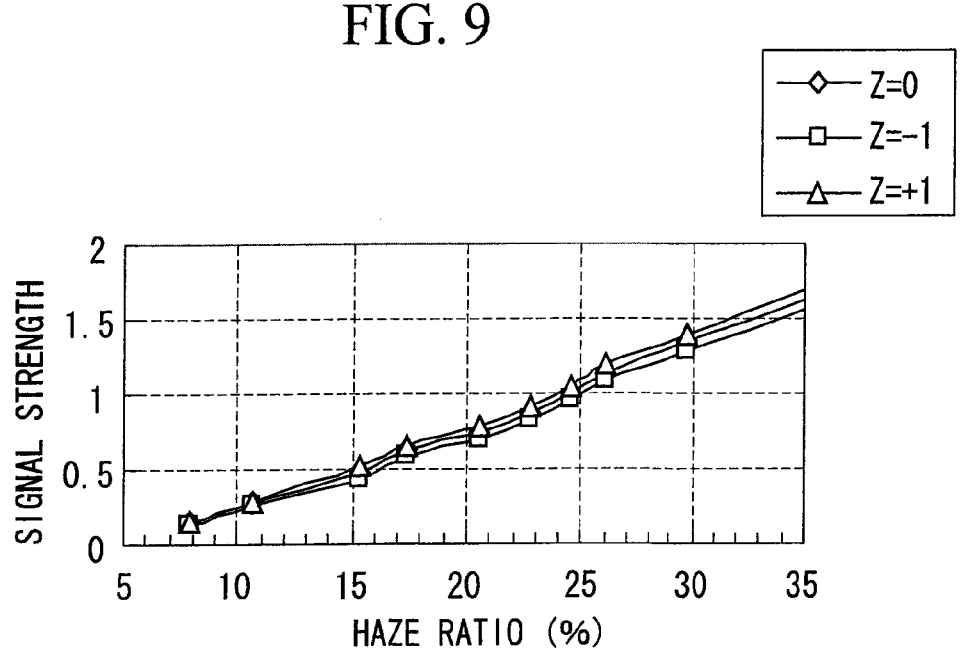
FIG. 9 is a figure showing haze ratio characteristics obtained by a preliminary test conducted for determining arrangement parameters.
Figure 10:
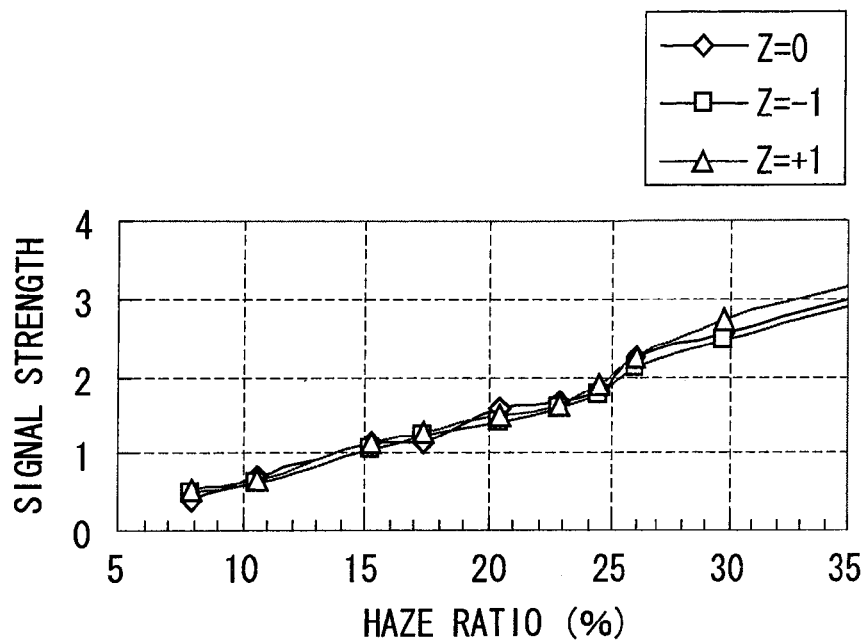
FIG. 10 is a figure showing haze ratio characteristics obtained by a preliminary test conducted for determining arrangement parameters.
Figure 11:
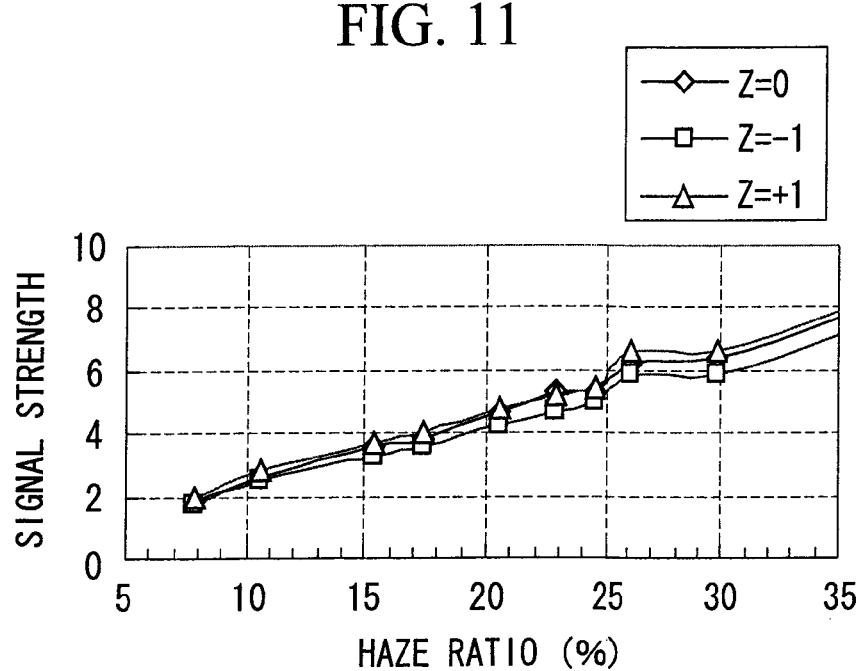
FIG. 11 is a figure showing haze ratio characteristics obtained by a preliminary test conducted for determining arrangement parameters.
Figure 12:
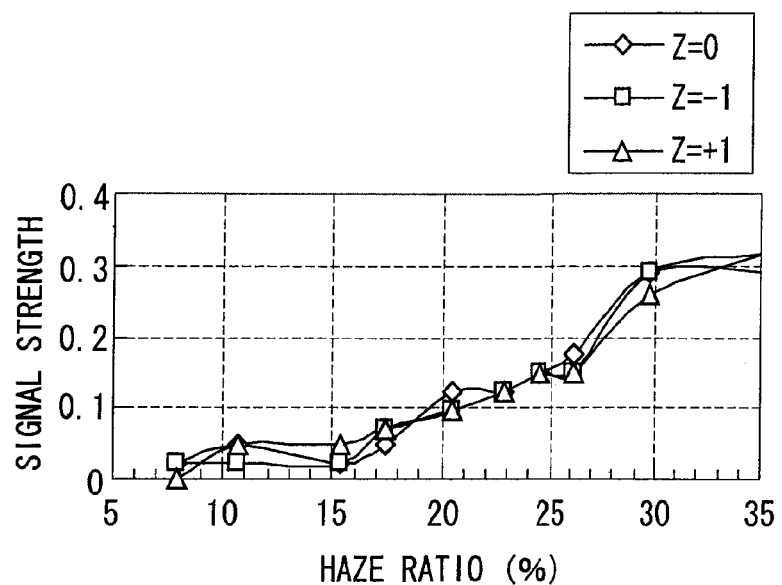
FIG. 12 is a figure showing haze ratio characteristics obtained by a preliminary test conducted for determining arrangement parameters.

As the respective representative examples, FIG. 7 shows the haze ratio characteristics when Da=5, θ=54°, wavelength λ=470 nm, L=25 mm, La=5 mm, Lb=5 mm, and Db=5 mm, FIG. 8 shows the haze ratio characteristics when Da=5 mm, θ=65°, wavelength λ=470 nm, L=40 mm, La=10 mm, Lb=5 mm, and Db=7 mm, FIG. 9 shows the haze ratio characteristics when Da=7 mm, θ=65°, wavelength λ=470 nm, L=30 mm, La=15 mm, Lb=10 mm, and Db=5 mm, FIG. 10 shows the haze ratio characteristics when Da=5 mm, θ=60°, wavelength λ=530 nm, L=40 mm, La=15 mm, Lb=5 mm, and Db=5 mm, FIG. 11 shows the haze ratio characteristics when Da=7 mm, θ=54°, wavelength λ=530 nm, L=40 mm, La=5 mm, Lb=15 mm, and Db=7 mm, and FIG. 12 shows the haze ratio characteristics when Da=5 mm, θ=65°, wavelength λ=590 nm, L=25 mm, La=5 mm, Lb=10 mm, and Db=7 mm.

In FIGS. 7 to 12, the vertical axis indicates the haze ratio and the horizontal axis indicates the signal strength (light intensity). In addition, in each figure, Z=0 represents the haze ratio characteristic when the test piece is placed on the reference position, Z=−1 represents the haze ratio characteristic when the test piece is positioned 1 mm closer to the light source 3a side from the reference position, and Z=+1 represents the haze ratio characteristic when the test piece at the reference position is shifted by 1 mm in the direction moving away from the light source 3a.

The haze ratio characteristic in which (1) the light intensity increases monotonically with the haze ratio, and (2) the maximum value of the amount of change in the light intensity due to the vertical shift of mounting position of the test piece is at most the first threshold value is extracted from among such haze ratio characteristics, and the arrangement parameters that are used for obtaining the extracted haze ratio characteristic are determined as the arrangement parameters to be used in the inspection.

Here, the above-mentioned first threshold value is a value that can be set arbitrarily depending on the required measuring accuracy. In addition, the maximum value Pmax of the amount of change in the light intensity due to the vertical shift of the mounting position of the test piece is obtained by, for example, in the haze ratio characteristics shown in FIG. 7, specifying the haze ratio at which the gap between the signal strengths in the respective haze ratio characteristics corresponding to Z=+1, 0, −1 are the largest, and calculating the difference between the maximum signal strength and the minimum signal strength at that haze ratio.

In the haze ratio characteristics shown in FIGS. 7 to 12, it is confirmed that all of the arrangement parameters satisfy the above-mentioned conditions (1) and (2). To determine the most suitable arrangement parameters among them, in the respective haze ratio characteristics, the signal-to-noise ratio and gradient β1 of the characteristics may be obtained, and the arrangement parameters that yield the largest values of the signal-to-noise ratio and the gradient may be selected. In particular, it is possible to ensure higher measurement sensitivity with a larger gradient β1.

FIG. 12 is a figure showing the haze ratio characteristics when light having the wavelength of 590 nm is used; it is shown that the light intensity increases substantially monotonically with the haze ratio, and the amount of change in the light intensity due to the vertical shift of the mounting position of the test piece is also small. Therefore, according to FIG. 12, it is demonstrated that the predetermined measuring accuracy can be ensured even when the wavelength of 590 nm is used in the inspection apparatus shown in FIG. 1.

[Second Parameter Setting Method]

In the above-described first parameter setting method, since the data has to be obtained by varying all arrangement parameters, the amount of data becomes enormous. Thus, in order to reduce the amount of data, it is considered to determine the arrangement parameters that are especially responsive to the vertical shift of the substrate from the above-mentioned arrangement parameters, and to obtain the appropriate parameter set values by varying values for only these arrangement parameters within the predetermined range.

For example, for the tube diameter Da of the light shielding hood attached to the light source 3a, in order to reduce the noise by blocking outside light as much as possible and in order to increase the directivity of the illumination light, it is preferable that the tube diameter be smaller. In addition, for the length La of this light shielding hood, since the light source 3a is required to be disposed at some distance away from the inspection-target substrate W, it is preferable that the length La be determined depending on the position at which this light source 3a is disposed. Such conditions can be derived not only on the basis of the vertical shift of the inspection-target substrate W, but also on the basis of the operating principle of the measurement system.

In addition, also for the length Lb of the light shielding hoods attached to the light receiving elements 2a, since outside light is required to be blocked as much as possible, it is preferable that the length Lb be set within a largest possible range to increase the shielding effect.

With this approach, for the lengths and tube diameters of the light shielding hoods of the light source 3a and the light receiving elements 2a, it is preferable to determine appropriate values on the basis of the conditions as described above, and therefore, it is preferable to determine the arrangement parameters related to the inclination angle θ of the light receiving element 2a, the wavelength λ of the light source 3a, and the distance L from the film surface to the light receiving element by performing specific tests.

In this embodiment, first of all, the values of the respective arrangement parameters that can be derived on the basis of the operating principle of the measurement system are set respectively as in the following.

Height La of the tubular light shielding hood of the light source 3a=15 mm

Tube diameter Da of the tubular light shielding hood of LED=5 mm

Length Lb of the tubular light shielding hood of the light receiving element=15 mm Tube diameter Db of the tubular light shielding hood of the light receiving element=7 mm In addition, for the distance L from the film surface of the transparent conductive film to the light receiving element and the inclination angle θ of the light receiving element, temporary set values, for example, distance L=40 mm and θ=54°, are set, the above-mentioned test piece is placed at the reference position in this measurement system, and the haze ratio characteristics are obtained while the wavelength λ of the light source is switched between 470 nm, 500 nm, 530 nm, 560 nm, and 590 nm, respectively.

Figure 13:
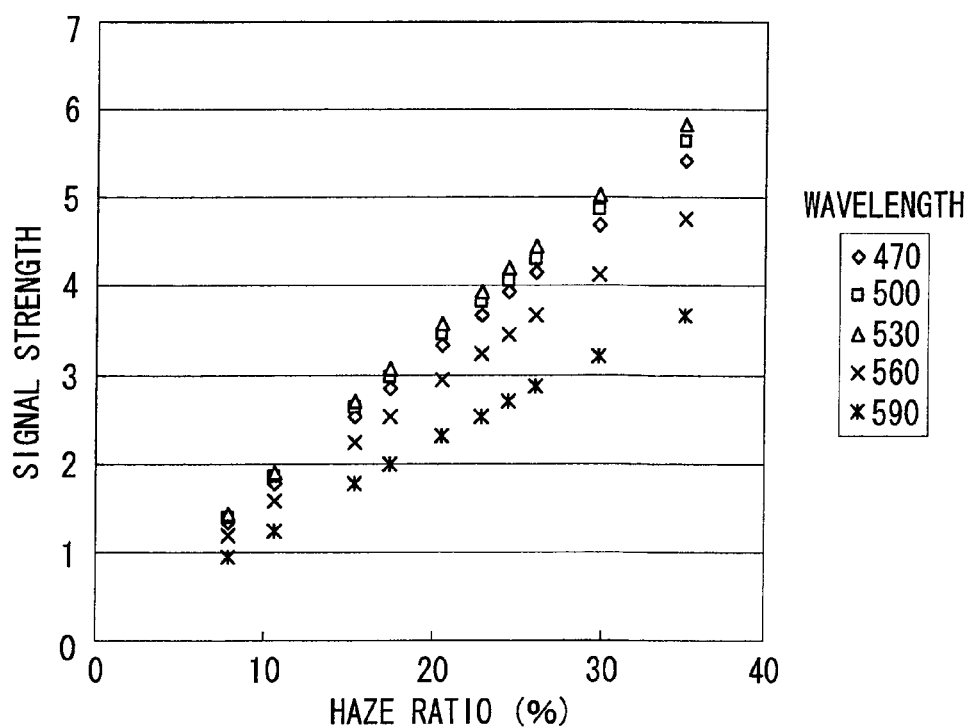
FIG. 13 is a figure showing haze ratio characteristics for the respective wavelengths when the wavelength of illumination light is set as a variable and the other arrangement parameters are fixed.

FIG. 13 shows the haze ratio characteristics. Here, when the haze ratio is to be obtained with high accuracy, it is desirable that the haze ratios and the light intensities be in a linear relationship, and in addition, it is preferable that the gradient β1 be larger. Therefore, in FIG. 13, the gradients β1 are calculated for all wavelengths and the respective gradients β1 are compared. For example, the characteristic with the gradient β1 is closely fit to a first-order curve, and the gradient at that time is obtained. As a result, it was found that the gradient β1 when the illumination light having the wavelength of 470 nm was used was the largest, and it is preferable to use light having the wavelength of 470 nm from the viewpoint of detection accuracy.

Figure 14:
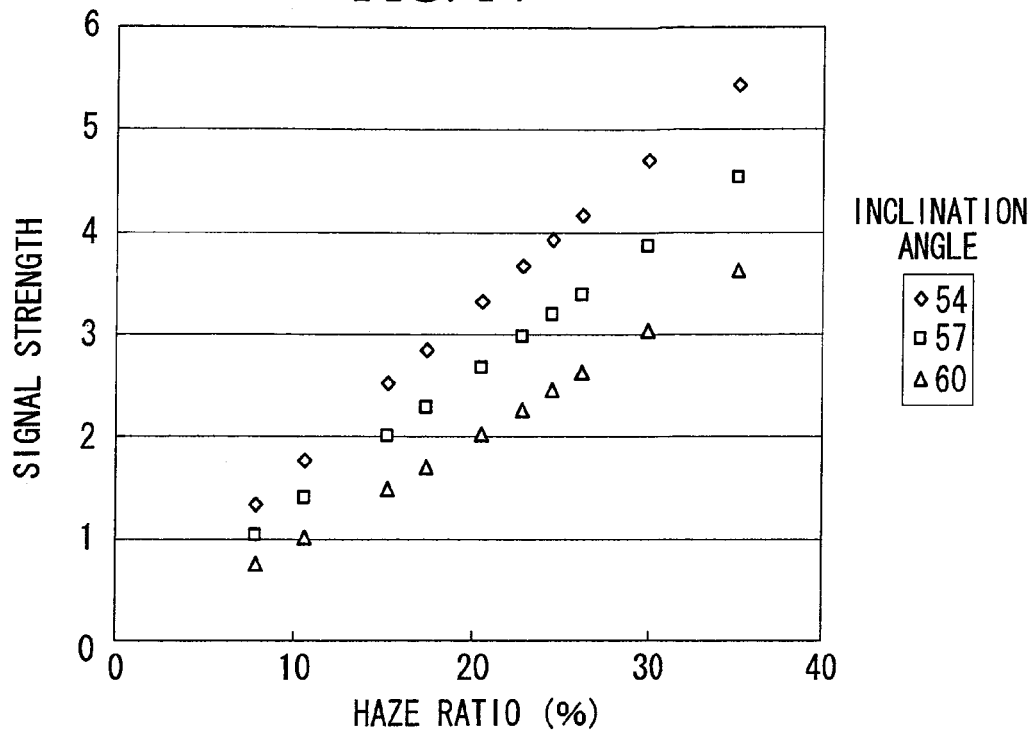
FIG. 14 is a figure showing haze ratio characteristics for the respective inclination angles when the inclination angle of a light receiving element is set as a variable and the other arrangement parameters are fixed.

Next, the inclination angle θ of the light receiving element 2a is set as variable, and the inclination angle θ of the light receiving element 2a that is the most suitable in the measurement system shown in FIG. 6 is determined within the predetermined range. Here, the light of 470 nm wavelength, which has been derived from FIG. 13, was used as the illumination light, and the other parameters of the measurement system were as described above. In this test, the inclination angle θ was varied to three values, 54°, 57°, and 60°, and the haze ratio characteristics were obtained respectively. FIG. 14 shows the haze ratio characteristics. In addition, the gradient β1 of the haze ratio characteristics at this time was obtained. As a result, it was found out that the gradient β1 was the largest when the inclination angle was 54°.

Next, the distance L from the film surface of the transparent conductive film through which the optical axis of the illumination light passes to the light receiving surface of the light receiving element is set as a variable, and a suitable distance L in the measurement system shown in FIG. 6 is determined within the predetermined range. Here, the light of 470 nm wavelength, which has been derived from FIG. 13, is used as the illumination light, and an angle of 54°, which has been derived from FIG. 14, is employed for the inclination angle θ of the light receiving element 2a. In addition, the other parameters of the measurement system are as described above.

Figure 15:
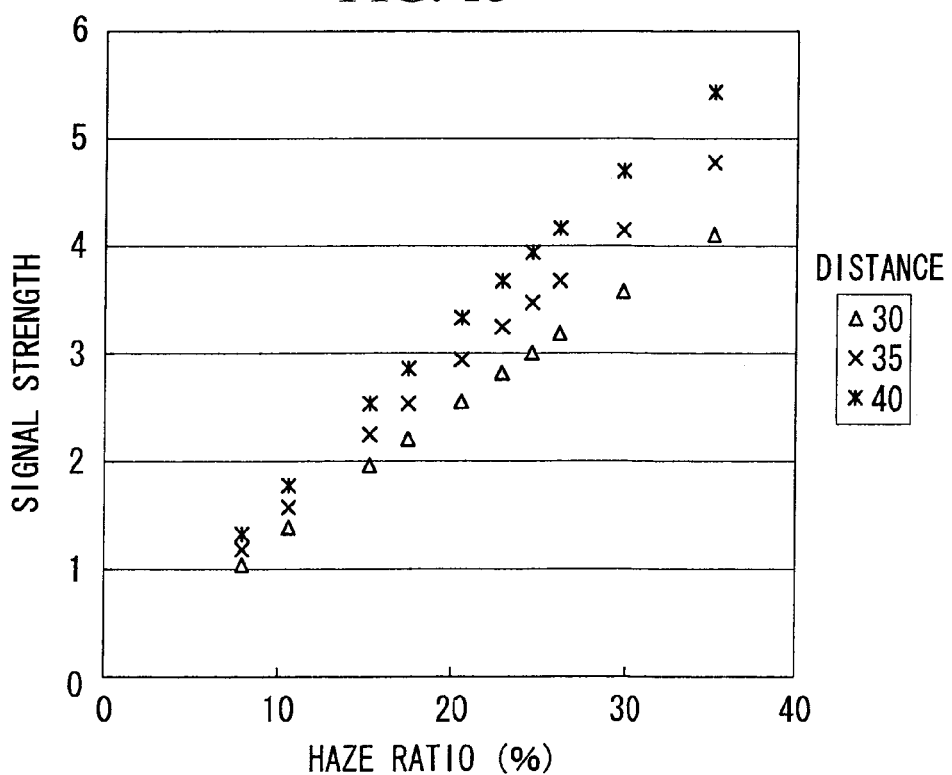
FIG. 15 is a figure showing haze ratio characteristics for the respective distances when the distance from a film surface to a light receiving element is set as a variable and the other arrangement parameters fixed.

In this test, the distance L was varied to three values, 30 mm, 35 mm, and 40 mm, and the respective haze ratio characteristics were obtained. FIG. 15 shows the haze ratio characteristics. In addition, the gradients β1 of the haze ratio characteristics at this time were obtained. As a result, it was found that the gradient β1 was the largest when the distance L was 40 mm.

From the above, it was found that high measuring accuracy can be achieved when the respective arrangement parameters of the measurement system are set as follows.

Figure 16:
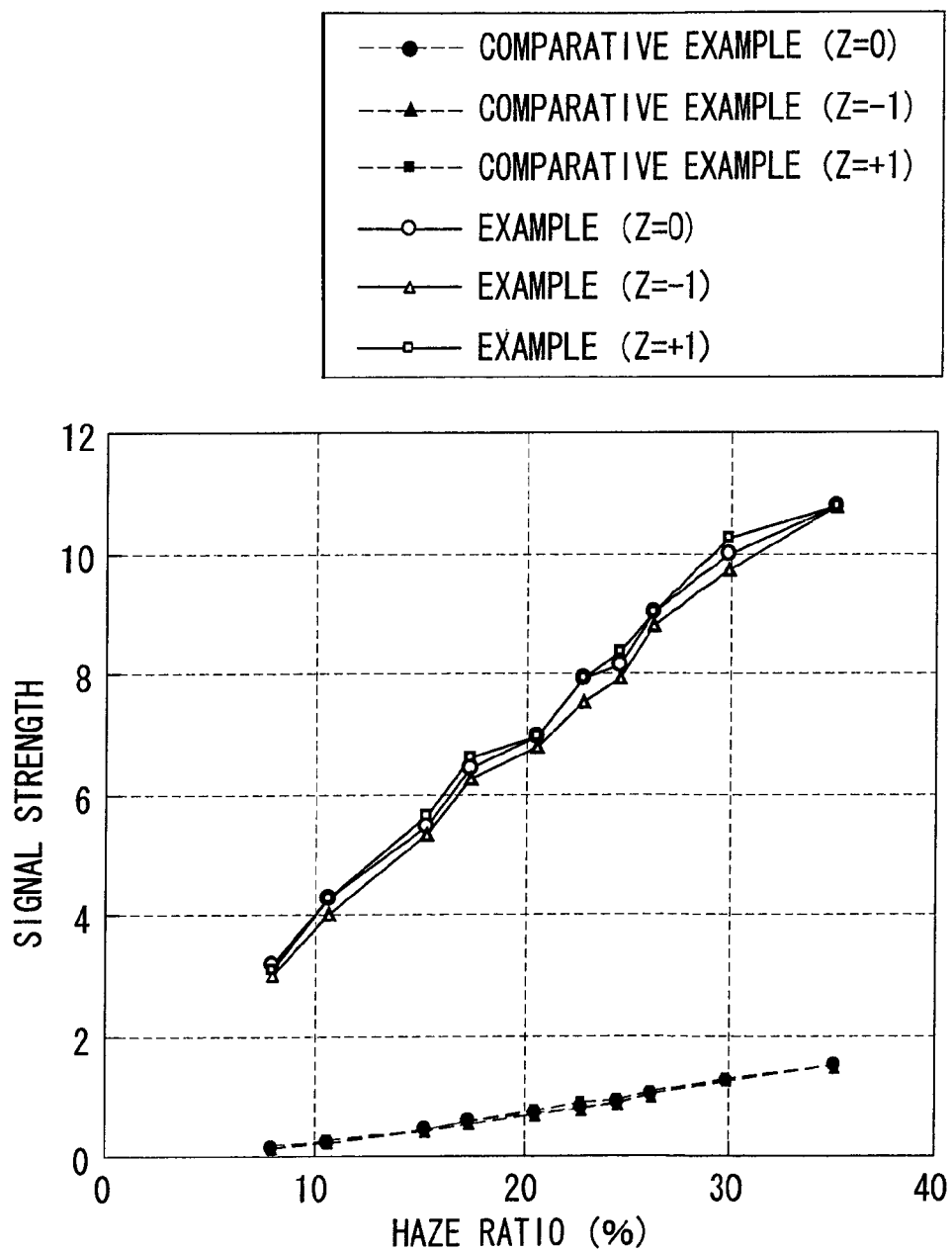
FIG. 16 is a figure showing haze ratio characteristics formed by using a measurement system that is set up using the arrangement parameters that have been determined to be the optimal in a preliminary test for determining arrangement parameters.

Height La of the tubular light shielding hood of the light source=15 mm
Tube diameter Da of the tubular light shielding hood of LED=5 mm
Distance L from the film surface of the transparent conductive film to the light receiving element=40 mm
Length Lb of the tubular light shielding hood of the light receiving element=15 mm
Tube diameter Db of the tubular light shielding hood of the light receiving element=7 mm
Inclination angle θ of the light receiving element=54°
Wavelength λ of the illumination light=470 nm Next, in the measurement system shown in FIG. 6, which was assembled by employing the above-mentioned arrangement parameters, the test piece was shifted vertically by 1 mm from the reference position, and the haze ratio characteristics at that time were obtained. FIG. 16 shows the haze ratio characteristics. As shown in FIG. 16, it was found that even when the position of the test piece was shifted by a predetermined distance along the optical axis of the illumination light, the haze ratio characteristics scarcely changed, and a high measurement sensitivity was achieved since a gradient β1 larger than that with the haze ratio characteristics shown as comparative examples was obtained. The comparative examples were obtained with the measurement system using the following arrangement parameters.

Height La of the tubular light shielding hood of the light source=10 mm
Tube diameter Da of the tubular light shielding hood of LED=7 mm
Distance L from the film surface of the transparent conductive film to the light receiving element=30 mm
Length Lb of the tubular light shielding hood of the light receiving element=10 mm
Tube diameter Db of the tubular light shielding hood of the light receiving element=7 mm
Inclination angle θ of the light receiving element=60°
Wavelength λ of the illumination light=530 nm As explained above, according to the thin-film inspection apparatus and the inspection method according to this embodiment, since single-wavelength light is radiated to the glass substrate side of the inspection-target substrate, the diffused transmitted light at that time is received by the light receiving elements, and the haze ratios of the transparent conductive film are obtained on the basis of the intensities of the light received, it is possible to obtain the haze ratios without being affected by the film thickness as in the related art.

FIG. 17 shows the results of measurements of the in-plane distribution of the haze ratios performed by the thin-film inspection apparatus shown in FIG. 1, built into a production line, while the inspection-target substrates are being transported. Here, four inspection-target substrates S were subjected to measurements, and 8×8=64 measurements points were set in the form of a grid in each of the inspection-target substrates S. The inspection-target substrates S were formed by forming a thin film on the transparent glass substrate; a thin film having a film thickness with an in-plane distribution (distribution range: about ±30%) was used. In addition, the haze ratios were also those having an in-plane distribution.

In addition, to verify the accuracy of the thin-film inspection apparatus, the inspection-target substrates were collected after the measurements, the inspection-target substrates were cut into small areas, and the haze ratios of the respective measurement points mentioned above were obtained with a commercial haze meter. The haze meter used conformed to JIS K 7136.

As shown in FIG. 17, according to the thin-film inspection apparatus according to this embodiment, even there were nonuniformities in the film thickness of the transparent conductive film, the average value of the measurement errors ΔHz of the haze ratios for four films was 1.4%, and it was found that measurement results with high reliability could be obtained. Here, ΔHz is a standard deviation (1 sigma) of the difference between the haze ratio obtained by the haze meter and the haze ratio obtained by the thin-film inspection apparatus of the present invention at the same measurement point, and the number of points N is 64.

According to this embodiment, the arrangement of the measurement system of the thin-film inspection apparatus is set to the values at which vibration of the inspection-target substrates is taken into account. Therefore, when the inspection apparatus is used by being built into an actual production line, it is possible to obtain highly reliable measurement results without being affected by the vertical shifts of the substrates. Furthermore, as shown in FIG. 16, for example, since the gradient β1 of the haze ratio characteristic used in the computer 7 is large, it is possible to obtain high measurement sensitivity.

In addition, by installing the thin-film inspection apparatus in a production line, it is possible to inspect all substrates on which the transparent conductive film has been formed, without delay, and when a defective item is detected, it is possible to remove the defective substrate from the production line during the process and to adjust the film forming conditions etc. for the transparent conductive film if required. In addition, even when the film formation fails due to a non-detectable problem in the film forming apparatus itself, it is possible to make a judgment immediately, enabling rapid recovery. In addition, by monitoring the formation of the transparent conductive film in an online manner, it is possible to maintain production of solar cells having a high electricity generation efficiency, and to remove defective substrates within a very short period of time when defects occur, thereby stabilizing the film formation quality and improving the production yield. Thus, it is possible to improve the production efficiency.

The thin-film inspection apparatus of the present invention can be widely applied to the areas of liquid crystal panels, semiconductor devices, and so forth, in which transparent conductive films and transparent optical films are used; however the area is not limited to that of thin film solar cells. In this case, the above-described light emitter 3 can be disposed at a position where the light can be radiated to the transparent conductive films and the transparent optical films that are formed on substrates being transported in the respective production processes, from the glass substrate side thereof, and the diffused transmitted light can be received by the photoreceptor 2.

{Reference Signs List}

1 transport conveyor
2 photoreceptor
2a light receiving element
3 light radiating apparatus
3a light source
4 light source power supply
7 computer
8 display device

The invention claimed is:

1. A thin-film inspection apparatus, comprising:
a light source that radiates single-wavelength light to an inspection-target substrate, which is formed by forming a thin film on a glass substrate from the glass substrate side;
a light receiving section that is disposed such that a light receiving axis intersects with an optical axis of illumination light emitted from the light source at a predetermined inclination angle and that receives diffused transmitted light that has been transmitted through the inspection-target substrate; and
a processor that obtains a haze ratio of the thin film on the basis of an intensity of light received by the light receiving section,
wherein the processor has a haze ratio characteristic that is made by associating the haze ratio and the light intensity of the diffused transmitted light and obtains the haze ratio by using the haze ratio characteristic and the intensity of the light received by the light receiving section, and
wherein in a case where a plurality of test pieces, which is formed by forming thin films having different haze ratios on glass substrates, is provided; the diffused transmitted light when the test piece is shifted vertically by a predetermined amount in an optical axial direction of the illumination light is received by the light receiving section; and the haze ratio characteristic is made by associating the light intensity and the haze ratio, the light receiving section is disposed at an inclination angle such that a relationship between the haze ratio and the light intensity is expressed as a monotonic increase or a monotonic decrease within a range of the haze ratios of the thin film to be inspected, and a maximum value of an amount of change in the light intensity due to a vertical shift of a mounting position of the test piece becomes a predetermined value or less.

2. A thin-film inspection apparatus according to claim 1, wherein the light source is disposed such that the optical axis of the illumination light emitted from the light source matches a normal direction of the inspection-target substrate.

3. A thin-film inspection apparatus according to claim 1, wherein the light source emits light having any wavelength from 350 nm or more to 760 nm or less.

4. A thin-film inspection apparatus according to claim 1, wherein the light source emits light having any wavelength from 350 nm or more to 590 nm or less.

5. A thin-film inspection apparatus according to claim 1, wherein when the light source emits light having any wavelength from 470 nm or more to 590 nm or less, an inclination angle of the light receiving section relative to the substrate surface of the inspection-target substrate is 54° or more to 65° or less.

6. A thin-film inspection apparatus according to claim 1, wherein
a first light shielding section is attached to the light source; and
a second light shielding section is attached to the light receiving section.

7. A thin-film inspection apparatus according to claim 1, wherein the inspection apparatus is built into a thin-film production line, and the light source is disposed at a position for radiating the illumination light to the inspection-target substrate, which is transported in the production line, from the glass substrate side.

8. A thin-film production system comprising the thin-film inspection apparatus according to claim 1, wherein the light source is disposed so as to radiate light to the inspection-target substrate, which is transported in a production line, from the glass substrate side.

9. A thin-film inspection method using a thin-film inspection apparatus according to claim 1 in which provides the haze ratio characteristic in advance, the method comprising steps of:
radiating single-wavelength light to the inspection-target substrate, which is formed by forming the thin film on the glass substrate from the glass substrate side;
receiving the diffused transmitted light that has passed through the inspection-target substrate; and
obtaining the haze ratio of the thin film by using the intensity of light received and the haze ratio characteristic.

10. A thin-film inspection apparatus, comprising:
a light source that radiates single-wavelength light to an inspection-target substrate, which is formed by forming a thin film on a glass substrate from the glass substrate side;
a light receiving section that is disposed such that a light receiving axis intersects with an optical axis of illumination light emitted from the light source at a predetermined inclination angle and that receives diffused transmitted light that has been transmitted through the inspection-target substrate; and
a processor that obtains a haze ratio of the thin film on the basis of an intensity of light received by the light receiving section,
wherein the processor has a haze ratio characteristic that is made by associating the haze ratio and the light intensity of the diffused transmitted light and obtains the haze ratio by using the haze ratio characteristic and the intensity of the light received by the light receiving section,
wherein a first light shielding section is attached to the light source,
wherein a second light shielding section is attached to the light receiving section, and
wherein when an inclination angle of the light receiving section, a size of an aperture at a light emitting side of the first light shielding section, a length from a tip of the light source to a tip of a light emitting end, a size of an aperture opposite the light receiving section in the second light shielding section, a length from a light receiving surface of the light receiving section to a tip of the aperture, and a distance from a position on an upper surface of the inspection-target substrate through which the optical axis of the illumination light passes to the light receiving surface of the light receiving section are set as arrangement parameters, these arrangement parameters are determined such that,
in a case where a plurality of test pieces, which is formed by forming thin films having different haze ratios on glass substrates, is provided; the diffused transmitted light when the test piece is shifted vertically by a predetermined amount in an optical axial direction of the illumination light is received by the light receiving section; and the haze ratio characteristic is made by associating the light intensity and the haze ratio, a relationship between the haze ratio and the light intensity is expressed as a monotonic increase or a monotonic decrease within a range of the haze ratio of the thin film to be inspected, and a maximum value of an amount of change in the light intensity due to a vertical shift of a mounting position of the test piece becomes a predetermined value or less.

11. A thin-film inspection apparatus according to claim 10, wherein the light source is disposed such that the optical axis of the illumination light emitted from the light source matches a normal direction of the inspection-target substrate.

12. A thin-film inspection apparatus according to claim 10, wherein the light source emits light having any wavelength from 350 nm or more to 760 nm or less.

13. A thin-film inspection apparatus according to claim 10, wherein the light source emits light having any wavelength from 350 nm or more to 590 nm or less.

14. A thin-film inspection apparatus according to claim 10, wherein when the light source emits light having any wavelength from 470 nm or more to 590 nm or less, an inclination angle of the light receiving section relative to the substrate surface of the inspection-target substrate is 54° or more to 65° or less.

15. A thin-film inspection apparatus according to claim 10, wherein, in a case where a plurality of test pieces, which is formed by forming thin films having different haze ratios on glass substrates, is provided; the diffused transmitted light when the test piece is shifted vertically by a predetermined amount in an optical axial direction of the illumination light is received by the light receiving section; and the haze ratio characteristic is made by associating the light intensity and the haze ratio, the light receiving section is disposed at an inclination angle such that a relationship between the haze ratio and the light intensity is expressed as a monotonic increase or a monotonic decrease within a range of the haze ratios of the thin film to be inspected, and a maximum value of an amount of change in the light intensity due to a vertical shift of a mounting position of the test piece becomes a predetermined value or less.

16. A thin-film inspection apparatus according to claim 10, wherein the inspection apparatus is built into a thin-film production line, and the light source is disposed at a position for radiating the illumination light to the inspection-target substrate, which is transported in the production line, from the glass substrate side.

17. A thin-film production system comprising the thin-film inspection apparatus according to claim 10, wherein the light source is disposed so as to radiate light to the inspection-target substrate, which is transported in a production line, from the glass substrate side.

18. A thin-film inspection method using a thin-film inspection apparatus according to claim 10 which provides the haze ratio characteristic in advance, the method comprising steps of:
radiating single-wavelength light to the inspection-target substrate, which is formed by forming the thin film on the glass substrate from the glass substrate side;
receiving the diffused transmitted light that has passed through the inspection-target substrate; and
obtaining the haze ratio of the thin film by using the intensity of light received and the haze ratio characteristic.

19. A method for determining an arrangement of a measurement system applied to a thin-film inspection apparatus according to claim 10, comprising:
when a wavelength of the light source, an inclination angle at which the light receiving section is disposed, a size of an aperture at a light emitting side of the first light shielding section, a length from a tip of the light source to a tip of a light emitting end, a size of an aperture opposite the light receiving section in the second light shielding section, a length from the light receiving surface of the light receiving section to a tip of the aperture, and a distance from a position on an upper surface of the inspection-target substrate through which the optical axis of the illumination light passes to the light receiving surface of a light receiving section are set as arrangement parameters,
a first step in which a plurality of test pieces, which is formed by forming thin films having different haze ratios on glass substrates is provided;
a second step in which, in the measurement system where the parameters are varied within predetermined ranges, each of which has been determined for every parameter, the diffused transmitted light is received by the light receiving section when the test pieces are shifted vertically by a predetermined amount in an optical axial direction of the illumination light;
a third step in which haze ratio characteristics are made by associating the light intensity of the diffused transmitted light and the haze ratio obtained in the second step, and these haze ratio characteristics are associated with respective parameter set values of the measurement system when the haze ratio characteristics are obtained;
a fourth step in which a haze ratio characteristic is extracted from a plurality of the haze ratio characteristics made in the third step, such that a relationship between the haze ratio and the light intensity is expressed as a monotonic increase or a monotonic decrease within a range of the haze ratio of the thin film to be inspected, and a maximum value of an amount of change in the light intensity due to a vertical shift of a mounting position of the test piece is a predetermined value or less; and
a fifth step in which the parameters when the haze ratio characteristic that is extracted in the fourth step is obtained are employed as the arrangement parameters of the measurement system in the inspection.

20. A method for determining an arrangement of a measurement system applied to a thin-film inspection apparatus according to claim 6, comprising:
when a wavelength of the light source, an inclination angle at which the light receiving section is disposed, a size of an aperture at a light emitting side of the first light shielding section, a length from a tip of the light source to a tip of a light emitting end, a size of an aperture opposite the light receiving section in the second light shielding section, a length from the light receiving surface of the light receiving section to a tip of the aperture, and a distance from a position on an upper surface of the inspection-target substrate through which the optical axis of the illumination light passes to the light receiving surface of a light receiving section are set as arrangement parameters,
a first step in which a plurality of test pieces, which is formed by forming thin films having different haze ratios on glass substrates is provided;
a second step in which, in the measurement system where the parameters are varied within predetermined ranges, each of which has been determined for every parameter, the diffused transmitted light is received by the light receiving section when the test pieces are shifted vertically by a predetermined amount in an optical axial direction of the illumination light;
a third step in which haze ratio characteristics are made by associating the light intensity of the diffused transmitted light and the haze ratio obtained in the second step, and these haze ratio characteristics are associated with respective parameter set values of the measurement system when the haze ratio characteristics are obtained;
a fourth step in which a haze ratio characteristic is extracted from a plurality of the haze ratio characteristics made in the third step, such that a relationship between the haze ratio and the light intensity is expressed as a monotonic increase or a monotonic decrease within a range of the haze ratio of the thin film to be inspected, and a maximum value of an amount of change in the light intensity due to a vertical shift of a mounting position of the test piece is a predetermined value or less; and
a fifth step in which the parameters when the haze ratio characteristic that is extracted in the fourth step is obtained are employed as the arrangement parameters of the measurement system in the inspection.

21. A method for determining an arrangement of a measurement system applied to a thin-film inspection apparatus which includes:
a light source that radiates single-wavelength light to an inspection-target substrate, which is formed by forming a thin film on a glass substrate from the glass substrate side;
a light receiving section that is disposed such that a light receiving axis intersects with an optical axis of illumination light emitted from the light source at a predetermined inclination angle and that receives diffused transmitted light that has been transmitted through the inspection-target substrate; and
a processor that obtains a haze ratio of the thin film on the basis of an intensity of light received by the light receiving section,
wherein the processor has a haze ratio characteristic that is made by associating the haze ratio and the light intensity of the diffused transmitted light and obtains the haze ratio by using the haze ratio characteristic and the intensity of the light received by the light receiving section,
wherein a first light shielding section is attached to the light source, and
a second light shielding section is attached to the light receiving section,
the method comprising:
when a wavelength of the light source, an inclination angle at which the light receiving section is disposed, a size of an aperture at a light emitting side of the first light shielding section, a length from a tip of the light source to a tip of a light emitting end, a size of an aperture opposite the light receiving section in the second light shielding section, a length from the light receiving surface of the light receiving section to a tip of the aperture, and a distance from a position on an upper surface of the inspection-target substrate through which the optical axis of the illumination light passes to the light receiving surface of a light receiving section are set as arrangement parameters,
a first step in which a plurality of test pieces, which is formed by forming thin films having different haze ratios on glass substrates is provided;
a second step in which, in the measurement system where the parameters are varied within predetermined ranges, each of which has been determined for every parameter, the diffused transmitted light is received by the light receiving section when the test pieces are shifted vertically by a predetermined amount in an optical axial direction of the illumination light;
a third step in which haze ratio characteristics are made by associating the light intensity of the diffused transmitted light and the haze ratio obtained in the second step, and these haze ratio characteristics are associated with respective parameter set values of the measurement system when the haze ratio characteristics are obtained;
a fourth step in which a haze ratio characteristic is extracted from a plurality of the haze ratio characteristics made in the third step, such that a relationship between the haze ratio and the light intensity is expressed as a monotonic increase or a monotonic decrease within a range of the haze ratio of the thin film to be inspected, and a maximum value of an amount of change in the light intensity due to a vertical shift of a mounting position of the test piece is a predetermined value or less; and
a fifth step in which the parameters when the haze ratio characteristic that is extracted in the fourth step is obtained are employed as the arrangement parameters of the measurement system in the inspection.

\* \* \* \* \*